US008469915B2

(12) United States Patent
Johannison et al.

(10) Patent No.: US 8,469,915 B2
(45) Date of Patent: Jun. 25, 2013

(54) DEVICE FOR TREATMENT OF WOUNDS USING A WOUND PAD AND A METHOD FOR MANUFACTURING OF WOUND PADS

(75) Inventors: Ulf Johannison, Landvetter (SE); Sofia Frantzich, Mölnlycke (SE)

(73) Assignee: Molnlycke Health Care AB, Goteborg (SE)

( * ) Notice: Subject to any disclaimer, the term of this patent is extended or adjusted under 35 U.S.C. 154(b) by 110 days.

(21) Appl. No.: 12/936,754

(22) PCT Filed: Apr. 7, 2009

(86) PCT No.: PCT/SE2009/050364
§ 371 (c)(1),
(2), (4) Date: Oct. 7, 2010

(87) PCT Pub. No.: WO2009/126102

PCT Pub. Date: Oct. 15, 2009

(65) Prior Publication Data
US 2011/0028919 A1 Feb. 3, 2011

(30) Foreign Application Priority Data

Apr. 9, 2008 (SE) .................................. 0800804

(51) Int. Cl.
*A61F 13/00* (2006.01)
*C09J 5/02* (2006.01)

(52) U.S. Cl.
USPC ............. 602/900; 604/19; 604/304; 604/317; 604/358; 604/369; 602/41; 602/46; 34/397; 34/399; 34/481; 34/482; 156/307.3; 156/329; 428/312.6; 428/391; 428/396

(58) Field of Classification Search
USPC .................. 604/19, 289–293, 303–309, 317, 604/319, 358–402; 602/41–79, 900; 34/306, 34/312–343, 397–400, 443–447, 481–486; 156/247, 295, 306.6–307.3, 329
See application file for complete search history.

(56) References Cited

U.S. PATENT DOCUMENTS 3,742,952 A 7/1973 Magers .................... 128/278
3,981,084 A * 9/1976 Sobota ....................... 34/123
(Continued)

FOREIGN PATENT DOCUMENTS

CN 1571682 1/2005
CN 1740217 3/2006
(Continued)

OTHER PUBLICATIONS

Chariker, et al. "Effective management of incisional and cutaneous fistulae with closed suction wound drainage." Journal of Contemp. Surg., Jun. 1989, vol. 34, pp. 59-63.

(Continued)

*Primary Examiner* — Melanie Hand
*Assistant Examiner* — Joshua Lee
(74) *Attorney, Agent, or Firm* — Ballard Spahr LLP

(57) ABSTRACT

A device for treatment of wounds using reduced pressure is provided. The device includes a pump, a reservoir connected to said pump for collecting exudate from a wound, an inlet to the reservoir for connecting the reservoir with the wound so as to allow the pump to expose the wound to the reduced pressure, a wound pad to be arranged in the wound cavity, and a sealing covering the wound and the wound pad. The wound pad consists of an open-cell polyurethane foam which is fully impregnated with a soft hydrophobic silicone gel, and the foam has a hardness of 1.0-6.0 kPa measured according to ISO 3386-1 at at 40% compression The wound pad can be used with an absorbent member. A method is also provided for manufacturing the wound pad.

4 Claims, 8 Drawing Sheets

U.S. PATENT DOCUMENTS

| | | | | |
|---|---|---|---|---|
| 4,382,441 | A | 5/1983 | Svedman | 604/291 |
| 4,525,166 | A | 6/1985 | Leclerc | 604/133 |
| 4,921,704 | A | 5/1990 | Fabo | 424/446 |
| 4,969,880 | A | 11/1990 | Zamierowski | 604/305 |
| 5,352,508 | A | 10/1994 | Cheong | |
| 5,385,494 | A | 1/1995 | Wilhelmi | 441/74 |
| 5,540,922 | A * | 7/1996 | Fabo | 424/402 |
| 5,636,858 | A | 6/1997 | Argenta | 128/898 |
| 5,645,081 | A | 7/1997 | Argenta | 128/898 |
| 5,985,442 | A * | 11/1999 | Nagaya | 428/357 |
| 6,051,747 | A | 4/2000 | Lindqvist | 602/46 |
| 6,207,875 | B1 * | 3/2001 | Lindqvist et al. | 602/46 |
| 6,855,135 | B2 | 2/2005 | Lockwood | 604/313 |
| 2003/0040687 | A1 * | 2/2003 | Boynton et al. | 601/6 |
| 2006/0063846 | A1 * | 3/2006 | Kim | 521/54 |
| 2010/0196501 | A1 | 8/2010 | Areskoug | 424/409 |
| 2010/0286584 | A1 | 11/2010 | Areskoug | 602/46 |
| 2010/0324510 | A1 | 12/2010 | Andresen | 604/319 |

FOREIGN PATENT DOCUMENTS

| | | |
|---|---|---|
| KR | 100471924 | 2/2005 |
| SE | 0701546-4 | 12/2008 |
| WO | WO 93/19710 | 10/1993 |
| WO | WO 2006/025848 | 3/2006 |
| WO | WO 2009/126102 | 10/2009 |

OTHER PUBLICATIONS

Davydov, et al. "The Bacteriological and Cytological Assessment of Vacuum Therapy of Purulent Wounds." Vestnik Khirurgii, Oct. 1988, pp. 48-52 (published in English in The Kremlin Papers, Perspectives in Wound Care).

Davydov, et al. "Vacuum Therapy in the Treatment of Purulent Lactation Mastitis." Vestnik Khirurgii, Sep. 1986, pp. 66-70 (published in English in The Kremlin Papers, Perspectives in Wound Care).

Davydov, et al. "Concepts for Clinical Biological Management of the Wound Process in the Treatment of Purulent Wounds using Vacuum Therapy." Vestnik Khirurgii, Feb. 1991, pp. 132-135 (published in English in The Kremlin Papers, Perspectives in Wound Care).

Kostiuchenok, et al. "The Vacuum Effect in the Surgical Treatment of Purulent Wounds." Vestnik Khirurgii, Sep. 1986, pp. 18-21 (published in English in The Kremlin Papers, Perspectives in Wound Care).

Usupov, et al. "Active Wound Drainage." Vestnik Khirurgii, 1987, pp. 42-45 (published in English in The Kremlin Papers, Perspectives in Wound Care).

International Search Report and Written Opinion issued Jul. 14, 2009 for International Patent Application No. PCT/SE2009/050364, which was filed on Apr. 7, 2009 (Inventor—Johannison, et al.; Applicant—Mölnlycke Health Care AB; pp. 1-17).

International Preliminary Report on Patentability issued Oct. 12, 2010 for International Patent Application No. PCT/SE2009/050364, which was filed on Apr. 7, 2009 (Inventor—Johannison, et al.; Applicant—Mölnlycke Health Care AB; pp. 1-11).

PACER Listing of Docket Entries.

Stipulation of Dismissal; Sep. 16, 2008.

Deposition of Stephen J. Clarson, Ph.D.; Feb. 1, 2007.

Deposition of Stephen J. Clarson, Ph.D.; Mar. 6, 2008.

Markman Order; Jun. 21, 2007.

First Amended Complaint and Demand for Jury Trial; Jun. 15, 2006.

Preliminary Constructions of Defendants Medline Industries, Inc. and Ossur HF; Dec. 21, 2006.

Joint Claim Construction Statement; Jan. 16, 2007.

Exhibit A of Joint Claim Construction Statement—Parties' proposed constructions of each disputed claim term, phrase, or clause and support for such constructions; Jan. 16, 2007.

Exhibit B of Joint Claim Construction Statement—Summary of Opinions of Dr. Stephen J. Clarson; Jan. 16, 2007.

Claim Constructing Brief of Defendants Medline Industries, Inc. and Ossur HF; Feb. 7, 2007.

Mölnlycke Health Care AB and Mölnlycke Health Care US Opening Claim Construction Brief; Feb. 7, 2007.

Exhibit 1 of Mölnlycke Health Care AB and Mölnlycke Health Care US Opening Claim Construction Brief—U.S. Patent No. 6,051,747; Feb. 7, 2007.

Exhibit 2, Parts A-I of Mölnlycke Health Care AB and Mölnlycke Health Care US Opening Claim Construction Brief—Gentleheal® Marketing Materials; Feb. 7, 2007.

Exhibit 3 of Mölnlycke Health Care AB and Mölnlycke Health Care US Opening Claim Construction Brief—Excerpts of Technical Dictionaries in the Chemical and Medical Fields; Feb. 7, 2007.

Exhibit 4 Parts A-E of Mölnlycke Health Care AB and Mölnlycke Health Care US Opening Claim Construction Brief—Excerpts of General purpose dictionaries; Feb. 7, 2007.

Exhibit 5 Parts A-B of Mölnlycke Health Care AB and Mölnlycke Health Care US Opening Claim Construction Brief—U.S. Patent No. 7,154,017; Feb. 7, 2007.

Excerpts of Videotaped Deposition of Dr. Steven J. Clarson; Feb. 7, 2007.

Excerpts of Videotaped Deposition of Tomas T. Fabo; Feb. 7, 2007.

Responsive Claim Construction Brief of Defendants Medline Industries, Inc. and Ossur HF: Feb. 7, 2007.

Mölnlycke Health Care AB and Mölnlycke Health Care US Response to Medline Industries, Inc. and Ossur HF Opening Claim Construction Brief; Feb. 7, 2007.

Order; Jun. 21, 2007.

Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order; Nov. 5, 2007.

Exhibit A of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—U.S. Patent No. 6,051,747; Nov. 5, 2007.

Exhibit B of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Defendants Medline Industries, Inc. and Ossur HF Disclosure of Invalidity Contentions; Nov. 5, 2007.

Exhibit C of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order 13 Excerpts of Jan. 31, 2007 Videotaped Deposition of Tomas T. Fabo; Nov. 5, 2007.

Exhibit D of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Aug. 21, 2007 Videotaped Deposition of Tomas T. Fabo; Nov. 5, 2007.

Exhibit E of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Correspondence dated Oct. 8, 2007 from Mr. Baldassare Vinti to Mr. Steve Moore; Nov. 5, 2007.

Exhibit F of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Jul. 25, 2007 Hearing; Nov. 5, 2007.

Exhibit G of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Defendants' Objections and Responses to Plaintiffs' First Set of Continuing Interrogatories; Nov. 5, 2007.

Exhibit H of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Sep. 6, 2007 Deposition of Jonathan Primer; Nov. 5, 2007.

Exhibit I of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Sep. 27, 2007 Deposition of Hilmar Jannusson: Nov. 5, 2007.

Exhibit J of Mölnlycke Health Care AB and Mölnlycke Health Care US Consolidated Brief in Opposition to Defendants Medline Industries, Inc. and Ossur HF Cross-Motion to Amend and in Reply to Defendants Opposition to Motion for Protective Order—Plaintiffs' Objections to Notice of 30(b)(6) Depositions Concerning the Issues of Infringement, Validity, and Enforceability: Nov. 5, 2007.

Medline Industries, Inc. and Ossur HF Motion for Summary Judgment of Invalidity; Mar. 26, 2008.

Medline Industries, Inc. and Ossur HF Memorandum of Law in Support of Motion for Summary Judgment of Invalidity; Mar. 26, 2008.

Medline Industries, Inc. and Ossur HF Rule 56.1 Statement of Undisputed Material Facts; Mar. 26, 2008.

Declaration of Jennifer R. Scullion in Support of Medline Industries, Inc. and Ossur HF Motion for Summary Judgment of Invalidity; Mar. 26, 2008.

Exhibit A of Medline Industries, Inc. and Ossur HF Rule 56.1 Statement of Undisputed Material Facts—U.S. Patent No. 6,051,747; Mar. 26, 2008.

Exhibit B of Medline Industries, Inc. and Ossur HF Rule 56.1 Statement of Undisputed Material Facts—U.S. Patent No. 4,921,704; Mar. 26, 2008.

Exhibit C of Medline Industries, Inc. and Ossur HF Rule 56.1 Statement of Undisputed Material Facts—U.S. Patent No. 5,340,363; Mar. 26, 2008.

Exhibit D of Medline Industries, Inc. and Ossur HF Rule 56.1 Statement of Undisputed Material Facts—EP Patent No. 0 261 167; Mar. 26, 2008.

Exhibit E of Medline Industries, Inc. and Ossur HF Rule 56.1 Statement of Undisputed Material Facts—U.S. Patent No. 5,540,922; Mar. 26, 2008.

Exhibit F of Medline Industries, Inc. and Ossur HF Rule 56.1 Statement of Undisputed Material Facts—U.S. Patent No. 5,635,201; Mar. 26, 2008.

Exhibit G of Medline Industries, Inc. and Ossur HF Rule 56.1 Statement of Undisputed Material Facts—British Patent No. 898,826; Mar. 26, 2008.

Exhibit H of Medline Industries, Inc. and Ossur HF Rule 56.1 Statement of Undisputed Material Facts—Excerpts of Jan. 31, 2007 Videotaped Deposition of Tomas T. Fabo; Mar. 26, 2008.

Exhibit I of Medline Industries, Inc. and Ossur HF Rule 56.1 Statement of Undisputed Material Facts—Excerpts of Aug. 21, 2007 Videotaped Deposition of Tomas T. Fabo; Mar. 26, 2008.

Exhibit J of Medline Industries, Inc. and Ossur HF Rule 56.1 Statement of Undisputed Material Facts—Excerpts of Videotaped Deposition of Dr. Steven J. Clarson; Mar. 26, 2008.

Exhibit K of Medline Industries, Inc. and Ossur HF Rule 56.1 Statement of Undisputed Material Facts—Excerpts of Videotaped Deposition of Craig Broussard, Ph.D., R.N; Mar. 26, 2008.

Exhibit L of Medline Industries, Inc. and Ossur HF Rule 56.1 Statement of Undisputed Material Facts—Excerpts of Videotaped Deposition of Larry Bogart; v.

Exhibit M of Medline Industries, Inc. and Ossur HF Rule 56.1 Statement of Undisputed Material Facts—Excerpts of the Prosecution File of U.S. Patent No. 6,051,747; Mar. 26, 2008.

Exhibit N of Medline Industries, Inc. and Ossur HF Rule 56.1 Statement of Undisputed Material Facts—Excerpts of the Prosecution File of U.S. Patent No. 6,051,747; Mar. 26, 2008.

Exhibit O of Medline Industries, Inc. and Ossur HF Rule 56.1 Statement of Undisputed Material Facts—Excerpts of the Prosecution File of U.S. Patent No. 6,051,747; Mar. 26, 2008.

Exhibit P of Medline Industries, Inc. and Ossur HF Rule 56.1 Statement of Undisputed Material Facts—Excerpts of the Prosecution File of U.S. Patent No. 6,051,747; Mar. 26, 2008.

Exhibit Q of Medline Industries, Inc. and Ossur HF Rule 56.1 Statement of Undisputed Material Facts—Initial Memorandum of the Fabo Interference Proceeding; Mar. 26, 2008.

Exhibit R of Medline Industries, Inc. and Ossur HF Rule 56.1 Statement of Undisputed Material Facts—Sua Sponte Holding of Unpatentability in View of Prior Art; Mar. 26, 2008.

Exhibit S of Medline Industries, Inc. and Ossur HF Rule 56.1 Statement of Undisputed Material Facts—Mölnlycke Health Care AB and Mölnlycke Health Care US Supplemental Answers to Defendant Ossur HF's First Set of Interrogatories; Mar. 26, 2008.

Exhibit T of Medline Industries, Inc. and Ossur HF Rule 56.1 Statement of Undisputed Material Facts—Mölnlycke Health Care AB and Mölnlycke Health Care US Response to Medline Industries, Inc. and Ossur HF Claim Construction Brief; Mar. 26, 2008.

Expert Declaration of Dr. Michael A. Brook in Support of Medline Industries, Inc. and Ossur HF Motion for Summary Judgment; Mar. 26, 2008.

Exhibit A of Expert Declaration of Dr. Michael A. Brook in Support of Medline Industries, Inc. and Ossur HF Motion for Summary Judgment—Curriculum Vitae; Mar. 26, 2008.

Exhibit B of Expert Declaration of Dr. Michael A. Brook in Support of Medline Industries, Inc. and Ossur HF Motion for Summary Judgment—Expert Report of Michael A. Brook, Ph. D. on Validity Issues; Mar. 26, 2008.

Mölnlycke Health Care AB and Mölnlycke Health Care US Motion for Partial Summary Judgment That U.S. Patent 6,051,747 is Not Invalid; Mar. 26, 2008.

Placeholder for Brief in Support of Mölnlycke Health Care AB and Mölnlycke Health Care US Motion for Partial Summary Judgment That U.S. Patent 6,051,747 is Not Invalid Filed Under Seal Pursuant to Revised Protective Order Submitted to the Court on Sep. 21, 2007; Mar. 26, 2008.

Mölnlycke Health Care AB and Mölnlycke Health Care US Statement of Undisputed Material Facts in Support of Motion to Strike Medline Industries, Inc. and Ossur HF New and Untimely Non-infringing Alternative Theory, Including Exhibits 1-9 Filed Under Seal Pursuant to Revised Protective Order; Mar. 26, 2008.

Excerpts of Videotaped Deposition of Andrew Martin Reed, Ph.D.; Mar. 26, 2008.

Excerpts of Videotaped Deposition of Laura Shafer; Mar. 26, 2008.

Excerpts of Videotaped Deposition of Craig Broussard, Ph.D., R.N; Mar. 26, 2008.

Excerpts of Videotaped Deposition of Larry Bogart; Mar. 26, 2008.

Placeholder for Exhibit 6—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 7—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 8—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Excerpts of Jan. 31, 2007 Videotaped Deposition of Tomas T. Fabo; Mar. 26, 2008.

Placeholder for Exhibit 10—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 11—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 12—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 13—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 14—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 15—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 16—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Excerpts of Videotaped Deposition of James Wetrich; Mar. 26, 2008.

Placeholder for Exhibit 18—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 19—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Placeholder for Exhibit 20—Mölnlycke Health Care AB and Mölnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.

Excerpts of Deposition of Michael Brook; Mar. 26, 2008.

Mölnlycke Health Care AB and Mölnlycke Health Care US Brief in Opposition to Medline Industries, Inc. and Ossur HF Motion for Summary Judgment of Invalidity; Apr. 24, 2008.

Exhibit 23 of Mölnlycke Health Care AB and Mölnlycke Health Care US Brief in Opposition to Medline Industries, Inc. and Ossur HF Motion for Summary Judgment of Invalidity—Excerpts of videotaped deposition of Andrew Martin Reed, Ph. D.; Apr. 24, 2008.

Exhibit 24 of Mölnlycke Health Care AB and Mölnlycke Health Care US Brief in Opposition to Medline Industries, Inc. and Ossur HF Motion for Summary Judgment of Invalidity—Excerpts of Deposition of Michael Brook; Apr. 24, 2008.

Exhibit 25 of Mölnlycke Health Care AB and Mölnlycke Health Care US Brief in Opposition to Medline Industries, Inc. and Ossur HF Motion for Summary Judgment of Invalidity—Excerpts of Videotaped Deposition of Dr. Steven J. Clarson; Apr. 24, 2008.

Exhibit 26 of Mölnlycke Health Care AB and Mölnlycke Health Care US Brief in Opposition to Medline Industries, Inc. and Ossur HF Motion for Summary Judgment of Invalidity—Excerpts of Videotaped Deposition of Larry Bogart; Apr. 24, 2008.

Exhibit 27 of Mölnlycke Health Care AB and Mölnlycke Health Care US Brief in Opposition to Medline Industries, Inc. and Ossur HF Motion for Summary Judgment of Invalidity—Excerpts of Deposition of Benoit Castel; Apr. 24, 2008.

Exhibit 28 of Mölnlycke Health Care AB and Mölnlycke Health Care US Brief in Opposition to Medline Industries, Inc. and Ossur HF Motion for Summary Judgment of Invalidity—*Ortho-McNeil Pharm., Inc* v. *Mylan Labs.,Inc.*, No. 2007-1223, 2008 WL 834402, at *5 (Fed. Cir. Mar. 31, 2008); Apr. 24, 2008.

Exhibit 29 of Mölnlycke Health Care AB and Mölnlycke Health Care US Brief in Opposition to Medline Industries, Inc. and Ossur HF Motion for Summary Judgment of Invalidity—Excerpts of Jan. 31, 2007 Videotaped Deposition of Tomas T. Fabo; Apr. 24, 2008.

Exhibit 30 of Mölnlycke Health Care AB and Mölnlycke Health Care US Brief in Opposition to Medline Industries, Inc. and Ossur HF Motion for Summary Judgment of Invalidity—Excerpts of Videotaped Deposition of Craig Broussard, Ph.D., R.N; Apr. 24, 2008.

Exhibit 31 of Mölnlycke Health Care AB and Mölnlycke Health Care US Brief in Opposition to Medline Industries, Inc. and Ossur HF Motion for Summary Judgment of Invalidity—Excerpts of the Prosecution File of U.S. Patent No. 6,051,747; Apr. 24, 2008.

Declaration of Stephen J. Clarson, Ph.D.; Apr. 24, 2008.

Declaration of Tomas Fabo dated Apr. 24, 2008; Apr. 24, 2008.

Exhibit A of Declaration of Tomas Fabo—Sua Sponte Holding of Unpatentability in View of Prior Art; Apr. 24, 2008.

Exhibit B of Declaration of Tomas Fabo—Fabo Opposition to the Sua Sponte Holding of Unpatentability in View of Prior Art; Apr. 24, 2008.

Exhibit C of Declaration of Tomas Fabo—Declaration of Tomas Fabo dated Oct. 30, 1991; Apr. 24, 2008.

Exhibit D of Declaration of Tomas Fabo—Opinion on the Final Hearing before the Board of Patent Appeals and Interferences; Apr. 24, 2008.

Declaration of Larry Bogart; Apr. 24, 2008.

Exhibit A of Declaration of Larry Bogart—U.S. Patent No. 5,856,245; Apr. 24, 2008.

Exhibit B of Declaration of Larry Bogart—U.S. Patent No. 5,352,508; Apr. 24, 2008.

Medline Industries, Inc. and Ossur HF Memorandum of Law in Opposition to Mölnlycke's Motion for Partial Summary Judgment; Apr. 24, 2008.

1. Medline Industries, Inc. and Ossur HF Response to Mölnlycke Health Care AB and Mölnlycke Health Care US Statement of Undisputed Material Facts, and 2. Medline Industries, Inc. and Ossur HF Counter-Statement of Additional Material Facts; Apr. 24, 2008.

Declaration of Jennifer R. Scullion in Support of Medline Industries, Inc. and Ossur HF Opposition to Mölnlycke's Motion for Partial Summary Judgment; Apr. 24, 2008.

Exhibit U of Declaration of Jennifer R. Scullion in Support of Medline Industries, Inc. and Ossur HF Opposition to Mölnlycke's Motion for Partial Summary Judgment—U.S. Patent No. 5,409,472; Apr. 24, 2008.

Exhibit V of Declaration of Jennifer R. Scullion in Support of Medline Industries, Inc. and Ossur HF Opposition to Mölnlycke's Motion for Partial Summary Judgment—U.S. Patent No. 5,571,529; Apr. 24, 2008.

Exhibit W of Declaration of Jennifer R. Scullion in Support of Medline Industries, Inc. and Ossur HF Opposition to Mölnlycke's Motion for Partial Summary Judgment—UK Patent Application GB 2 290 031; Apr. 24, 2008.

Exhibit X of Declaration of Jennifer R. Scullion in Support of Medline Industries, Inc. and Ossur HF Opposition to Mölnlycke's Motion for Partial Summary Judgment—U.S. Patent No. 3,972,328; Apr. 24, 2008.

Exhibit Y of Declaration of Jennifer R. Scullion in Support of Medline Industries, Inc. and Ossur HF Opposition to Mölnlycke's Motion for Partial Summary Judgment—U.S. Patent No. 5,209,965; Apr. 24, 2008.

Exhibit Z of Declaration of Jennifer R. Scullion in Support of Medline Industries, Inc. and Ossur HF Opposition to Mölnlycke's Motion for Partial Summary Judgment—U.S. Patent No. 5,445,604; Apr. 24, 2008.

Exhibit AA of Declaration of Jennifer R. Scullion in Support of Medline Industries, Inc. and Ossur HF Opposition to Mölnlycke's Motion for Partial Summary Judgment—U.S. Patent No. 5,098,500; Apr. 24, 2008.

Exhibit BB of Declaration of Jennifer R. Scullion in Support of Medline Industries and Ossur HF Opposition to Mölnlycke's Motion for Partial Summary Judgment—U.S. Patent No. 3,364,063; Apr. 24, 2008.

Exhibit CC of Declaration of Jennifer R. Scullion in Support of Medline Industries and Ossur HF Opposition to Mölnlycke's Motion for Partial Summary Judgment—U.S. Patent No. 5,782,787; Apr. 24, 2008.

Exhibit DD of Declaration of Jennifer R. Scullion in Support of Medline Industries and Ossur HF Opposition to Mölnlycke's Motion for Partial Summary Judgment—U.S. Patent No. 4,629,457; Apr. 24, 2008.

Exhibit EE of Declaration of Jennifer R. Scullion in Support of Medline Industries and Ossur HF Opposition to Mölnlycke's Motion for Partial Summary Judgment—U.S. Patent No. 3,645,835; Apr. 24, 2008.

Exhibit FF of Declaration of Jennifer R. Scullion in Support of Medline Industries and Ossur HF Opposition to Mölnlycke's Motion for Partial Summary Judgment—U.S. Patent No. 4,454,191; Apr. 24, 2008.

Exhibit GG of Declaration of Jennifer R. Scullion in Support of Medline Industries and Ossur HF Opposition to Mölnlycke's Motion for Partial Summary Judgment—U.S. Patent No. 4,773,409; Apr. 24, 2008.

Exhibit HH of Declaration of Jennifer R. Scullion in Support of Medline Industries and Ossur HF Opposition to Mölnlycke's Motion for Partial Summary Judgment—Great Britain Patent No. 439,085; Apr. 24, 2008.

Exhibit II of Declaration of Jennifer R. Scullion in Support of Medline Industries and Ossur HF Opposition to Mölnlycke's Motion for Partial Summary Judgment—European Patent No. 0 230 387; Apr. 24, 2008.

Exhibit JJ of Declaration of Jennifer R. Scullion in Support of Medline Industries and Ossur HF Opposition to Mölnlycke's Motion for Partial Summary Judgment—US Patent No. 3,349,676; Apr. 24, 2008.

Exhibit KK of Declaration of Jennifer R. Scullion in Support of Medline Industries and Ossur HF Opposition to Mölnlycke's Motion for Partial Summary Judgment—US Patent No. 4,838,253; Apr. 24, 2008.

Exhibit LL of Declaration of Jennifer R. Scullion in Support of Medline Industries and Ossur HF Opposition to Mölnlycke's Motion for Partial Summary Judgment—US Patent Application 2004/0127839; Apr. 24, 2008.

Exhibit MM of Declaration of Jennifer R. Scullion in Support of Medline Industries and Ossur HF Opposition to Mölnlycke's Motion for Partial Summary Judgment—Excerpts from the Jan. 31, 2007 Videotaped Deposition of Tomas Fabo.

Exhibit NN of Declaration of Jennifer R. Scullion in Support of Medline Industries and Ossur HF Opposition to Mölnlycke's Motion for Partial Summary Judgment—Excerpts from the Aug. 21, 2007 Video Deposition of Tomas Fabo; Apr. 24, 2008.

Exhibit OO of Declaration of Jennifer R. Scullion in Support of Medline Industries and Ossur HF Opposition to Mölnlycke's Motion for Partial Summary Judgment—Excerpts from the Videotaped Deposition of Steven Clarson; Apr. 24, 2008.

Exhibit PP of Declaration of Jennifer R. Scullion in Support of Medline Industries and Ossur HF Opposition to Mölnlycke's Motion for Partial Summary Judgment—Excerpts from the Videotaped Deposition of Craig Broussard; Apr. 24, 2008.

Exhibit QQ of Declaration of Jennifer R. Scullion in Support of Medline Industries and Ossur HF Opposition to Mölnlycke's Motion for Partial Summary Judgment—Excerpts from the Videotaped Deposition of Larry Bogart; Apr. 24, 2008.

Exhibit RR of Declaration of Jennifer R. Scullion in Support of Medline Industries and Ossur HF Opposition to Mölnlycke's Motion for Partial Summary Judgment—Excerpts from the Videotaped Deposition of Baldur Baldursson; Apr. 24, 2008.

Exhibit SS of Declaration of Jennifer R. Scullion in Support of Medline Industries and Ossur HF Opposition to Mölnlycke's Motion for Partial Summary Judgment—Excerpts from the Videotaped Deposition of Laura Shafer; Apr. 24, 2008.

Exhibit TT of Declaration of Jennifer R. Scullion in Support of Medline Industries and Ossur HF Opposition to Mölnlycke's Motion for Partial Summary Judgment—Excerpts from the Deposition of Hilmar Janusson; Apr. 24, 2008.

Exhibit VV of Declaration of Jennifer R. Scullion in Support of Medline Industries and Ossur HF Opposition to Mölnlycke's Motion for Partial Summary Judgment—Excerpts from the Oct. 8, 2007 deposition of Bengt Lindquist; Apr. 24, 2008.

Exhibit WW of Declaration of Jennifer R. Scullion in Support of Medline Industries and Ossur HF Opposition to Mölnlycke's Motion for Partial Summary Judgment—Excerpts from the Videotaped Deposition of Palmar Gudnason; Apr. 24, 2008.

Exhibit XX of Declaration of Jennifer R. Scullion in Support of Medline Industries and Ossur HF Opposition to Mölnlycke's Motion for Partial Summary Judgment—Excerpts from the Feb. 28, 2008 Deposition of Michael Brook; Apr. 24, 2008.

Exhibit YY of Declaration of Jennifer R. Scullion in Support of Medline Industries, Inc. and Ossur HF Opposition to Mölnlycke's Motion for Partial Summary Judgment—Excerpts from the Videotaped Deposition of Andrew Martin Reed, Ph. D.; Apr. 24, 2008.

Exhibit ZZ of Declaration of Jennifer R. Scullion in Support of Medline Industries, Inc. and Ossur HF Opposition to Mölnlycke's Motion for Partial Summary Judgment—Excerpts from the Video Deposition of Staffan Kuuse; Apr. 24, 2008.

Exhibit CCC of Declaration of Jennifer R. Scullion in Support of Medline Industries and Ossur HF Opposition to Mölnlycke's Motion for Partial Summary Judgment—Wound Care Project overview Exhibit No. 78; Apr. 24, 2008.

Exhibit DDD of Declaration of Jennifer R. Scullion in Support of Medline Industries and Ossur HF Opposition to Mölnlycke's Motion for Partial Summary Judgment—Medline's Production No. MED 001810 through 001816; Exhibit No. 20; Apr. 24, 2008.

Exhibit LLL of Declaration of Jennifer R. Scullion in Support of Medline Industries and Ossur HF Opposition to Mölnlycke's Motion for Partial Summary Judgment—Ossur's Production No. OS 046840 through 046851; Ulman et al., "Silicone Pressure Sensitive Adhesives for Healthcare Applications."; Apr. 24, 2008.

Exhibit MMM of Declaration of Jennifer R. Scullion in Support of Medline Industries and Ossur HF Opposition to Mölnlycke's Motion for Partial Summary Judgment—Excerpt from the file for Patent Interference Proceeding No. 102,565; Apr. 24, 2008.

Exhibit NNN of Declaration of Jennifer R. Scullion in Support of Medline Industries and Ossur HF Opposition to Mölnlycke's Motion for Partial Summary Judgment—Staffan Areskoug's Deposition Exhibit No. 6; "Design Input AiO-Dressing"; Apr. 24, 2008.

Expert Declaration of Dr. Michael A. Brook in Support of Medline Industries and Ossur HF Opposition to Mölnlycke Health Care AB and Mölnlycke Health Care US Motion for Partial Summary Judgment ; Apr. 24, 2008.

Exhibit C of Expert Declaration of Dr. Michael A. Brook in Support of Medline Industries and Ossur HF Opposition to Mölnlycke Health Care AB and Mölnlycke Health Care US Motion for Partial Summary Judgment—Expert Report of Michael A. Brook, Ph. D. on Validity Issues; Apr. 24, 2008.

Declaration of Andrew M. Reed, Ph.D. in Support of Medline Industries and Ossur HF Opposition to Mölnlycke Health Care AB and Mölnlycke Health Care US Motion for Partial Summary Judgment; Apr. 24, 2008.

Exhibit A of Declaration of Andrew M. Reed, Ph.D. in Support of Medline Industries and Ossur HF Opposition to Mölnlycke Health Care AB and Mölnlycke Health Care US Motion for Partial Summary Judgment—Curriculum Vitae of Andrew M. Reed; Apr. 24, 2008.

Exhibit B of Declaration of Andrew M. Reed, Ph.D. in Support of Medline Industries and Ossur HF Opposition to Mölnlycke Health Care AB and Mölnlycke Health Care US Motion for Partial Summary Judgment—Expert Report of Andrew M. Reed, Ph. D.; Apr. 24, 2008.

Mölnlycke Health Care AB and Mölnlycke Health Care US Reply Brief to Medline Industries and Ossur HF Opposition to Motion for Partial Summary Judgment that U.S. Patent No. 6,051,747 is Not Invalid; May 23, 2008.

Excerpts of Feb. 1, 2007 Videotaped Deposition of Dr. Steven J. Clarson; May 23, 2008.

Excerpts of Videotaped Deposition of Stefan Areskoug; May 23, 2008.

Excerpts of Mar. 6, 2008 Videotaped Deposition of Dr. Steven J. Clarson (Taken by Medline Industries and Ossur HF); May 23, 2008.

Excerpts of Aug. 21, 2007 Video Deposition of: Mr Tomas Fabo; May 23, 2008.

Exhibit 36 of Mölnlycke Health Care AB and Mölnlycke Health Care US Reply Brief to Medline Industries and Ossur HF Opposition to Motion for Partial Summary Judgment that U.S. Patent No. 6,051,747 Is Not Invalid; Filed Under Seal Pursuant to Protective Order; May 23, 2008.

Excerpts of Videotaped Deposition of James Wetrich; May 23, 2008.
Excerpts of Videotaped Deposition of Laura Shafer; May 23, 2008.
Excerpts of Videotaped Deposition of Craig Broussard, Ph.D., R.N.; May 23, 2008.
Excerpts of Videotaped Deposition of Larry Bogart; May 23, 2008.
Excerpts of Video Deposition of Staffan Kuuse; May 23, 2008.
Exhibit 42 of Mölnlycke Health Care AB and Mölnlycke Health Care US Reply Brief to Medline Industries and Ossur HF Opposition to Motion for Partial Summary Judgment that U.S. Patent No. 6,051,747 is Not Invalid; Filed Under Seal Pursuant to Protective Order; May 23, 2008.
Excerpts of Video Deposition of Elisabet Lundqvist; May 23, 2008.
Second Declaration of Larry Bogart; May 23, 2008.
Expert Report of Mr. Larry Bogart dated Dec. 28, 2007; May 23, 2008.
Medline Industries and Ossur HF Reply Memorandum in Support of Motion for Summary Judgment of Invalidity; May 23, 2008.
Appendix of Unreported Authorities; May 23, 2008.
Excerpts from Manual of Patent Examining Procedure (Jul. 1997 Revisions); May 23, 2008.
Transcript of Videotaped Deposition of Tomas T. Fabo on Jan. 31, 2007 (215 pages); Jan. 31, 2007.
Transcript of Videotaped Deposition of James Wetrich (199 pages); Jan. 31, 2007.
Search Report issued on Oct. 25, 2012 for Chinese Patent Application No. CN 200980112322, which was filed on Apr. 7, 2009 [Inventor—Johannison; Applicant—Mölnlycke Health Care AB] [2 pages].

* cited by examiner

DEVICE FOR TREATMENT OF WOUNDS USING A WOUND PAD AND A METHOD FOR MANUFACTURING OF WOUND PADS

CROSS REFERENCE TO RELATED APPLICATIONS

The present application is a National Phase Application of International Application No. PCT/SE2009/050364, filed Apr. 7, 2009, which claims priority to Swedish Patent Application No. 0800804-7, filed Apr. 9, 2008, which applications are incorporated herein fully by this reference.

TECHNICAL FIELD

The present invention concerns a device for treatment of wounds using reduced pressure, said device comprising
a pump capable of providing a reduced pressure,
a reservoir connected to said pump for collecting exudate from a wound,
an inlet to the reservoir for connecting the reservoir with the wound so as to allow the pump to expose the wound to the reduced pressure, a wound pad to be arranged in the wound cavity and a sealing covering the wound and said wound pad. The invention also concerns a device for treatment of wounds, said device comprising a wound pad to be arranged in the wound cavity, an absorbent member for collecting exudate from a wound and a sealing covering the wound, said wound pad and said absorbent member. In addition the invention concerns a method for manufacturing of a wound pad of an open-cell polyurethane foam which is fully impregnated with a soft hydrophobic silicone gel.

BACKGROUND ART

Several methods are earlier known for treatment of difficult wounds, such as infected wounds, diabetes wound, pressure sore or deep wounds.

Drainage of for instance operation wounds or other liquid discharging wounds with the aid of negative pressure is a standard treatment that has been used for decades. An example of a manual suction pump for said use is described in U.S. Pat. No. 3,742,952.

In said publication is described a pump in form of an elastically compressible body of an open-cell foam, preferably a polyurethane foam. Said body also serves as a canister for exudate drained from the wound. It is stated that the pump has a capacity to hold a negative pressure of 15-80 mmHg more than 48 hours. A drainage tube is arranged with a perforated end part in the wound cavity and via tube connected to the pump.

A similar device is described in U.S. Pat. No. 4,525,166. In the description of said publication is specifically stated that the negative pressure in addition to drain wound fluids from the wound also presses the edges of the wound together, thereby stimulating rapid tissue granulation and healing of the wound. The two mentioned publication thus teach that vacuum treatment of wounds stimulates the healing of the wounds.

The terms vacuum treatment, treatment at a reduced pressure and treatment with negative pressure are alternatively used in the literature. When using any of this terms in the present description the terms always concern treatment at pressure below normal atmospheric pressure.

Treatment of deep wounds have earlier also been performed by adding an irrigation liquid to the wound and then draining the injected liquid and pus and bacteria present in the wound before the irrigation. Examples of such devices are described in U.S. Pat. No. 5,385,494 and U.S. Pat. No. 4,382,441.

Extensive investigations of the effect of continuous and intermittent treatment of wounds under negative pressure, i.e. pressure below atmospheric pressure, were performed in the 1980's at Russian institutes. One was able to establish that difficult and normally slow-healing wounds healed considerably faster with the aid of vacuum treatment compared with conventional treatment.

One was inter alia also able to show that treatment at a reduced pressure provides a significant antibacterial effect. Said Russian investigations are described in several articles in the Russian medical journal Vestnik Khirurgii. The relevant articles from said journal are:
1) Kostiuchenok et al, September 1986, pages 18-21.
2) Davydov et al, September 1986, pages 66-70.
3) Usupov et al, April 1987, pages 42-45.
4) Davydov et al, Oktober 1988, pages 48-52.
5) Davydov et al, Februari 1991, pages 132-135.

In an article by Chariker et al in the journal Contemporary Surgery, No. 34, June 1989 is stated that vacuum treatment stimulate tissue granulation and contraction of wounds, which with conventional treatment are very difficult to heal.

Vacuum treatment of wounds is also described in U.S. Pat. Nos. 4,969,880, 5,645,081, 5,636,643, 6,855,135 B2 and WO 2006/025848 A2.

Hitherto known devices for vacuum treatment of wounds are not satisfactory in every respect. For instance U.S. Pat. No. 5,645,081 describes a wound pad in form of an open-cell foam. It is believed that cell growth are stimulated when tissue can grow into the pores of the foam but there is also a risk that the formed tissue fasten in the pores and is damaged when the pad is removed from the wound. There is a demand to improve wound pads for use in severe and deep wounds.

Disclosure of Invention

By means of the present invention an improved device of the type mentioned in the introduction has been achieved. The device in accordance with the invention is characterized in that the wound pad consist of an open-cell polyurethane foam which is fully impregnated with a soft hydrophobic silicone gel, and that the foam has a hardness of 1.0-6.0 kPa measured according to ISO 3386-1 at 40% compression.

According to an embodiment the invention is further characterized in that the density of the foam is 20-40 kg/m$^3$, and preferably 25-35 kg/m$^3$ measured according to ISO 845.

According to an embodiment the invention is characterized in that the foam at 25% elongation has a wet elasticity higher than 6 kPa and a dry elasticity higher than 13 kPa measured according to a method described in Appendix A.

According to an embodiment the invention is characterized in that the silicone gel is homogeneously distributed over the cross-section of the pad of open-cell foam.

According to an embodiment of the invention the open-cell foam is fully impregnated with silicone gel as approved by observing photos taken with an Electron Probe Micro Analyser with Energy Dispersive Spectrometer (EPMA/EDS), such as JEOL, model JXA-8600.

According to an embodiment the invention is further characterized in that the cell diameter is between 500-1800 µm, such as between 1100-1500 µm measured according to Visiocell SS-T.013.4E. Foam of this type is sold by for instance the Belgian firm Recticel.

The inventive concept is the specific wound pad intended to be arranged in a wound cavity. The invention also concerns a device for treatment of wounds without using reduced pressure. According to a modified embodiment, i.e. without using reduced pressure, a device comprising a wound pad to be arranged in the wound cavity, an absorbent member for collecting exudate from a wound and a sealing covering the wound, said wound pad and said absorbent member is characterized in that the wound pad consist of an open-cell polyurethane foam which is fully impregnated with a soft hydrophobic silicone gel, and that the foam has a hardness of 1.0-6.0 kPa measured according to ISO 3386-1 at 40% compression.

Said foam is according to an embodiment further characterized in that the cell diameter is between 500-1800 μm, and preferably 1100-1500 μm measured according to Visiocell SS-T.013.4E.

The present invention also concerns a method for manufacturing the wound pad. The method according to the invention is characterized in that silicone gel in uncured state is applied on one side of a web of said foam, that said web with the applied silicone gel is fed between two webs of process paper through a pair of press rolls, between which press rolls the foam with the applied silicone gel is squeezed for distributing the gel over the total cross section of the foam, that said two webs of process paper with excessive silicone gel from the foam web are removed from the foam web and that the foam web thereafter is heated for curing of the silicone gel.

According to an embodiment the method is further characterized in that the curing of the silicone gel is performed in a hot blast furnace at a temperature of about 100° C. during about 1-5 minutes, preferably about 3 minutes.

According to an embodiment the method is characterized in that the pressure between the press rolls is about 5 bar and that said pressure is adjustable for optimal impregnation and that control of full impregnation of the foam web is performed by inspecting the two webs of process paper, which both paper webs are coated with silicone gel when the foam web is fully impregnated.

BRIEF DESCRIPTION OF DRAWINGS

The invention will be described in greater detail below with reference to illustrative embodiments which are shown in the accompanying drawings, in which.

EMBODIMENT(S) OF THE INVENTION

Figure 1:
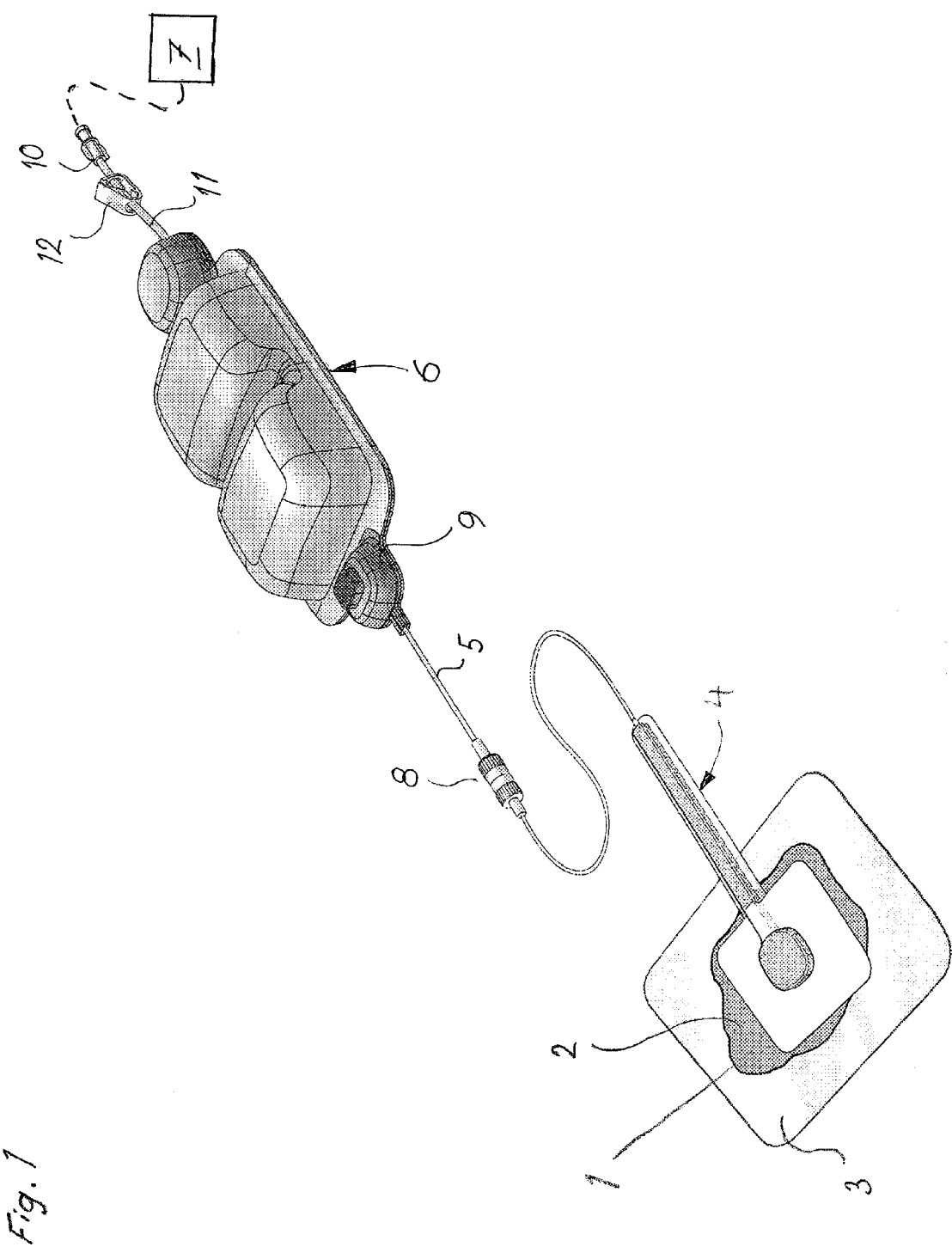
FIG. 1 is a schematic view in perspective of a first embodiment of a device in accordance with the invention during use.

FIG. 1 shows the device in accordance with the invention during use. A wound 1 is schematically illustrated. Within the wound cavity is arranged a wound pad 2, for instance of an open-cell foam. A plastic film 3 serves as a sealing and covers the wound and the wound pad. The plastic film is adhered to the skin of the patient around the wound. A small aperture is arranged in said film over the wound and an adaptor 4 is arranged to connect the wound and the wound pad with an inlet tube 5 to a reservoir 6. The reservoir is connected to a suction pump, which is just schematically indicated at 7. The pump can be an electrical pump which is capable of providing a reduced pressure in the reservoir and wound of about 10-25 kPa.

The construction and function of the adaptor 4 and the sealing film 3 are described in detail in our co-pending Swedish patent application No. 0701546-4. Instead of describing said parts in detail we refer to said application, which contents are incorporated in the description of the present invention. The adaptor 4 is connected with the inlet tube 5 with a luer-lock connection 8.

The device in accordance with the present invention is intended to expose the wound to a reduced pressure in order to stimulate the healing of the wound. The device in accordance with the invention is provided with a leakage indicator 9, which is arranged to indicate when the pressure within the reservoir exceeds a predetermined pressure. In FIG. 1 is shown the female part 10 of a luer-lock connection on an outlet tube 11 from the reservoir. The outlet tube 11 which can be connected to a suction pump 7 and which is manufactured of a flexible plastic material, such as PVC, is provided with a lock clip 12. The lock clip is open when the outlet tube is connected with a suction pump and can be closed by the user or caretaker when the suction pump is disconnected from the device.

The reservoir 6 will be described with reference to FIG. 2. The reservoir includes a first compressible material 20 which is adapted to elastically expand after compression. The material 20 contains interconnected voids, With the expression "interconnected voids" is meant that air can pass all through the material. The purpose with this first material is to create a volume that can hold a reduced pressure for several hours after a suction source is disconnected. A suitable material is an open-cell foam, such as a high density polyurethane foam based on polyether polyol sold under the trade name Eurocel 130, which is extremely elastic and has a density of 110-130 $kg/m^3$ measured according to ISO 845. In the embodiment according to FIG. 2 the first material consists of a bottom piece 201 and two separated top pieces 202 and 203. The reservoir 6 also includes a second material, which is capable of absorbing wound fluids in an amount several times its own weight and retain it also under mechanical pressure. A suitable material is a super absorbent material under the trade name Pilotbond DT 360. This material is supplied in form of a fibrous web and is marked on the drawing with the reference 21. In the embodiment in accordance with FIG. 2 several layers of said superabsorbent web are applied on the opposite main sides of the first material 20.

The reservoir is enclosed in a cover, which comprises a bottom plate 22 of a relatively stiff material and a plastic film 23 joined to the bottom plate. An example of a suitable plastic film is a polyurethane film of a thickness of 150 μm. The plastic film 23 is arranged with extra material with regards to what is needed for an empty reservoir in order to allow the superabsorbent to swell when liquid is absorbed. As shown in FIG. 2 the plastic film 23 and the superabsorbent web are pressed down in the central part between the two top pieces 202,203 of the first material. With such a construction the reservoir gets a central hinge 204 which facilitates the fastening of the reservoir on a rounded body part of a user. The bottom plate 22 is in the shown embodiment arranged to serve as chassis for other parts of the device. An example of material for the bottom plate is polyurethane rubber. The choice of material in the bottom plate is however not critical. In the shown embodiment the leakage indicator 9 is arranged on the bottom plate. The inlet tube 5 extends in a channel in the bottom plate under the leakage indicator into the reservoir and ends with a one-way valve 24, which is arranged to allow gas and liquid to flow in the direction from the wound to the reservoir.

The first material 20, which in the shown embodiment is an open-cell PUR-foam, is enclosed in a breathable and liquid-tight layer 25. This layer forms a pouch around the first material, which pouch is open only at the end of the reservoir where the outlet tube 11 enters the reservoir. The outlet tube 11 enters the reservoir via a pocket 26 and is inserted inside the pouch and extends inside the pouch with its free end 110 close to the bottom 240 of said pouch. A purpose with the arrangement of the outlet tube inside the breathable and liquid-tight pouch is to hinder that liquid from the wound which enters the reservoir via said one-way valve 24 is sucked out through the outlet tube.

A third material 27, which have a high liquid spreading capability and which in the shown embodiment comprises two parts, are arranged to spread liquid absorbed by the reservoir over the major part of the reservoir. One of said parts encircles the top piece 202 and the just opposite part of the bottom piece 201 of the first material and the other encircles the top piece 203 and the just opposite part of the bottom piece 201. The liquid spreading third material 27 is as shown in FIG. 2 arranged outside the pouch 25.

Said second material 21 of a superabsorbent material is arranged in several layers on both major sides of the first material. The second material is arranged outside the third material and the pouch 25 and is thereby separated from the first material by said liquid spreading material and also by the breathable but liquid-tight pouch 25. The superabsorbent layers are just in front of the one-way valve 24 provided with through-holes 210. Liquid from the wound which is sucked into the reservoir through the one-way valve 24 will pass through said holes 210 and reach the liquid spreading material which effectively will spread the liquid all over the reservoir before the liquid is taken up by the superabsorbent material. This material is capable of absorbing wound fluids in an amount several times its own weight but has poor liquid spreading. The use of the spreading material 27 is therefore critical for the function. The webs of superabsorbent material, the second material 21, swell as they absorb liquid. As the plastic film 23 is arranged with extra material with regards to what is needed for an empty reservoir the superabsorbent can swell freely when liquid is absorbed until the available volume inside the cover is fully used. The compressible first material will absorb liquid first after the superabsorbent material is saturated with liquid. The free end 110 of the outlet tube is close to the bottom 250 of the liquid-tight pouch 25. Liquid can only enter the pouch through the opening 251. It is therefore highly unlikely that any liquid will enter the outlet tube through the free end 110. For safety a piece 31 of superabsorbent is applied within the outlet tube 11. A piece of the superabsorbent web as described above can be used. An elongated piece of said web which is twined and then inserted in the outlet tube forms an effective barrier for liquid. The superabsorbent will swell and hinder liquid to pass to the pump.

When a device in accordance with the invention is used on a wound of a patient the pump will create a reduced pressure, i.e. a pressure below atmospheric pressure, within the reservoir and the wound. The first compressible material will be compressed due to the reduced pressure.

If one during wound treatment with reduced pressure wants to disconnect the pump this could be done without negatively affecting the treatment. The tube clip 12 is closed before disconnecting the pump. The compressed first material, the open-cell foam, will retain a reduced pressure within the reservoir and the wound when the pump is disconnected. The system will leak but this is compensated through the elastic expansion of the compressed material. The reservoir as described can for example be dimensioned so that the reduced pressure is maintained at an acceptable level for at least 10 hours. An acceptable level is that the negative pressure is not less than 60 mmHg. A suitable negative pressure during vacuum treatment is about 120-130 mmHg below atmospheric pressure. If the system is dimensioned to work satisfactorily for 10 hours the negative pressure should not decrease below 60 mmHg during this period.

The pocket 26 is arranged on the bottom plate 22 and is provided with an opening 260 through which the outlet tube and tube clip can be inserted into the pocket.

One essential problem with vacuum treatment of wound is as mentioned above that it is extremely difficult to maintain the intended reduced pressure in the wound due to air leakage.

A leakage indicator 9 is arranged to indicate when the pressure within the reservoir exceeds a predetermined pressure. The leakage indicator is fastened on the bottom plate 22. Channels 30 connect the interior of the reservoir with a space within the indicator.

Figure 3:
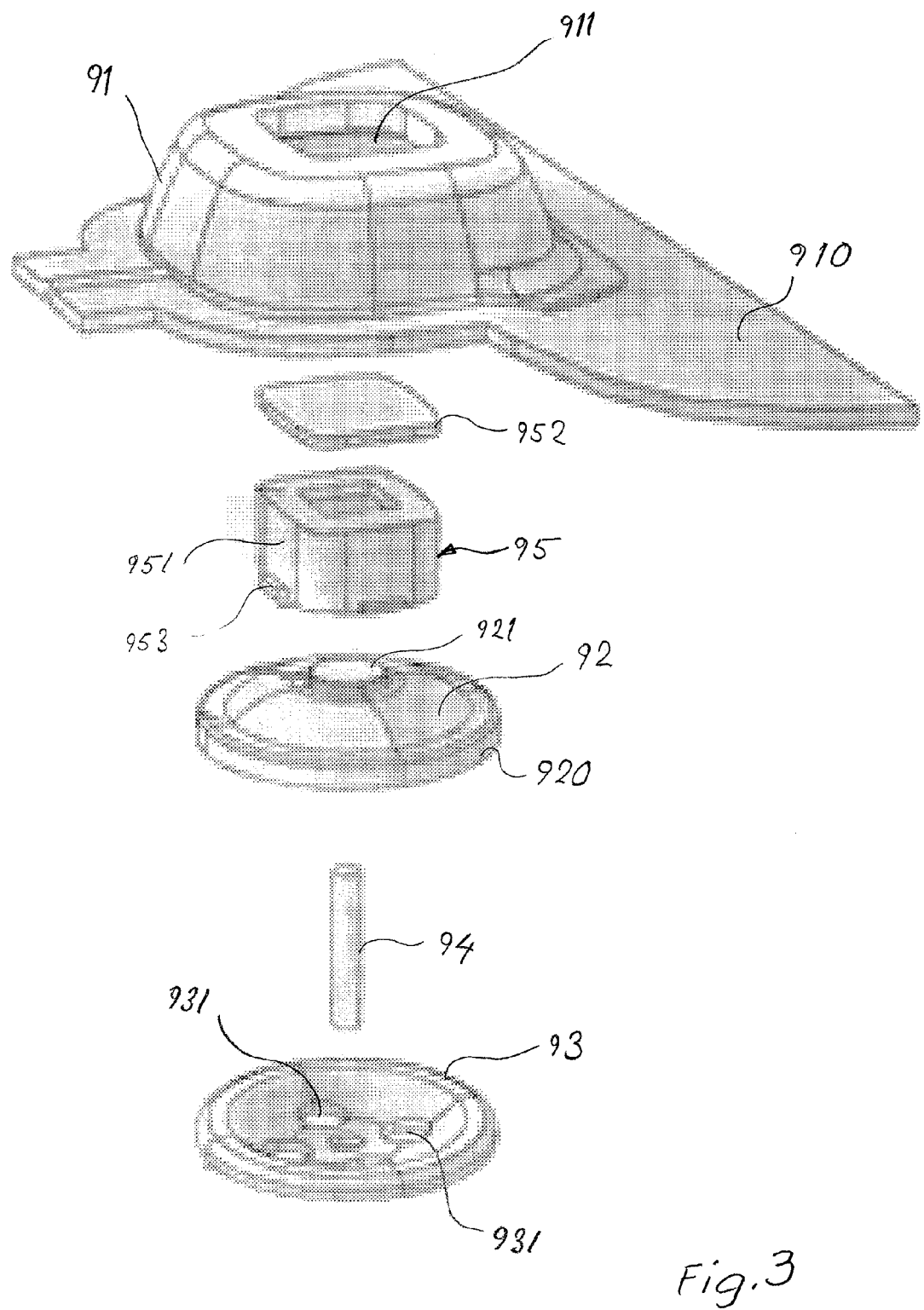
FIG. 3 is an exploded view of a detail of the device in accordance with FIGS. 1 and 2.

The construction and function of an embodiment of the leakage indicator will be described with reference to the exploded view in FIG. 3.

Figure 2:
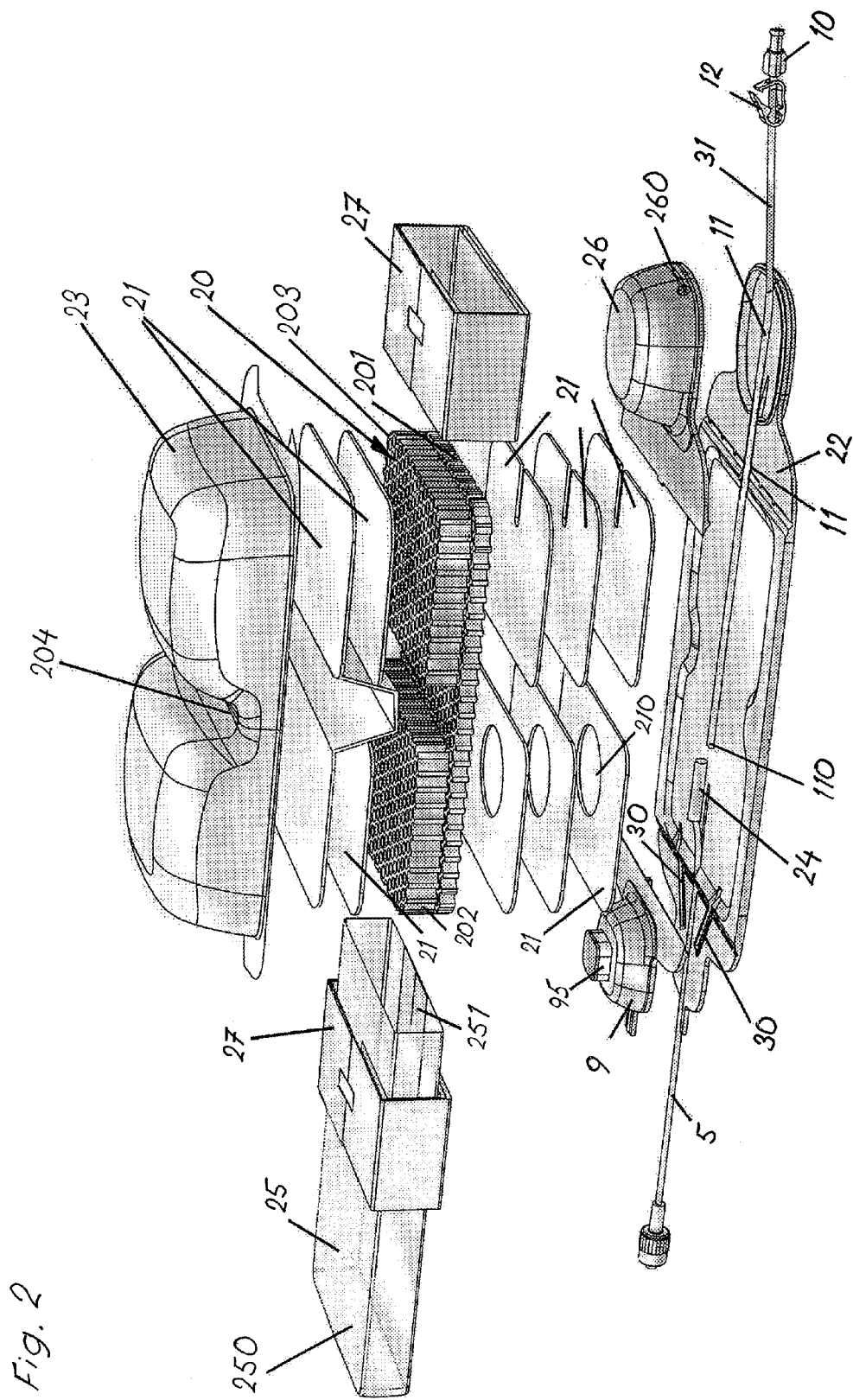
FIG. 2 is an exploded drawing of parts of the device in accordance with FIG. 1.

The leakage indicator 9 comprises a housing 91 with a base plate 910, which as shown in FIG. 2 is fastened on the bottom plate 22. The channels 30 in the bottom plate connect the interior of the reservoir with the interior of the housing 91.

Inside the housing is arranged a membrane 92, which covers a space connected with the inside of the reservoir, via said channels 30, and which is sealed around its periphery 920 to the surrounding inner wall of the housing. A foundation plate 93 with a bowl-shaped upper surface is arranged on the bottom plate 22. Holes 931 is arranged in the foundation plate 93 for connecting the space below the membrane 92 with the interior of the reservoir via said channels 30. A spring 94 is arranged in said space under the membrane. The spring is fastened between the foundation plate 93 and the membrane 92. The spring is arranged so that it is in unloaded state when the membrane is domed shaped as in FIG. 3.

An indicating button 95 is connected to the membrane 92 via a rod 921 which is fastened in the centre of the membrane and which has a cross section of such a small size that it only covers a minor part of the membrane. The indicating button comprises a bottom part 951 which has a colour that distinguish clearly from the housing 91. The indicating button has a top part 952 in a neutral colour and is provided with hooks 953 which are arranged to limit the buttons movement upwards through the opening 911 in the housing.

The leakage indicator is arranged to indicate when the pressure within the reservoir exceeds a predetermined pressure. The spring is arranged to cooperate with the pressure inside said space, i.e. the space below the membrane in the housing, against the atmospheric pressure such that said spring is arranged to be in compressed state when the pressure inside said space is at or below said predetermined pressure and that the spring is arranged to expand to bring the indicating button to become visible outside said surrounding wall of the housing 91 to indicate that the pressure inside the gas barrier exceeds said predetermined pressure.

An example of a suitable material in the membrane is a 80 μm thick film of PUR/EVOH/PUR where ethylene vinyl alcohol (EVOH) forms a gas barrier. Such a film is sold under the trade name Epurex LPT 9036. A suitable spring is spring No. 1128 from the company Lesjöfors Stockholms Fjäder AB.

Figure 4A:
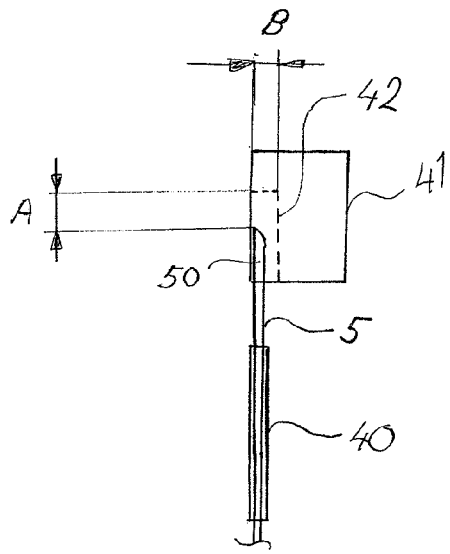
FIGS. 4a and 4b are schematic illustrations of a first example of the one-way valve at the inlet tube.
Figure 4B:
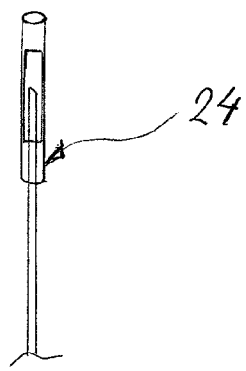

FIG. 4*a* shows how a first example of the one-way valve at the inlet tube can be manufactured. A tube 40 with a larger inner diameter than the outer diameter of the inlet tube is first treaded over the inlet tube. The outer diameter of the inlet tube is for instance about 2 mm. An advantage with such a thin tube compared with a thicker tube is that the tube can be sharply bent without any practical risk that the bending causes folds that block transportation of gas and liquid through the tube. A thin polyurethane film 41 coated with a silicone gel on one side is double folded over the end part 50 with gel against gel. The film 41 is suitably of a thickness of 20 μm and when applied of a size of 20×20 mm, i.e. a size that is manageable to handle. The folded film is adhered around the end part 50, with 10 mm on the tube 5 and 10 mm outside, and is cut along the broken line 42. The film is cut so that the folded film extends a distance A, suitably about 5 mm, outside the end of the tube and a distance B, of about 4 mm, sideways. The tube 40 is then treaded over the cut film so that the tube is arranged over the film as shown in FIG. 4*b*, i.e. extends about the same distance outside the both ends of the cut film. An example of a suitable silicone gel is a hydrophobic silicone gel marketed by Dow Corning under the trade name Dow-Corning Q7-22. A silicone gel layer of a thickness of 40 g/m² applied on the film 41 works for the intended purpose. The formed one-way valve works as follows.

When a reduced pressure is generated by the suction pump the valve membrane formed by the part of the film which extends the distance A outside the end of the tube 5 forms an open channel which allows suction of air and liquid from the wound. If the pressure inside the reservoir increase above the pressure in the wound there is no risk that wound exudate is sucked back to the wound. The valve membrane or the channel formed by the film part which extends outside the end of the tube 5 will be pressed together and close the channel when the pressure outside the channel formed by the thin film is higher than the pressure in the channel. The silicone gel on the inside of the channel walls will adhere together and form a tight seal. The outer tube 40 works as a shield around the channel formed by said film part and the film part forming the membrane is only affected by the air pressure between the wound and the reservoir, i.e. any mechanical pressure around the one-way valve will be taken up by the outer tube 40. The one-way valve will open again when the pressure in the reservoir is reduced under the pressure within the wound. The one-way valve 24 described above is also illustrated in FIG. 2.

Figure 5A:
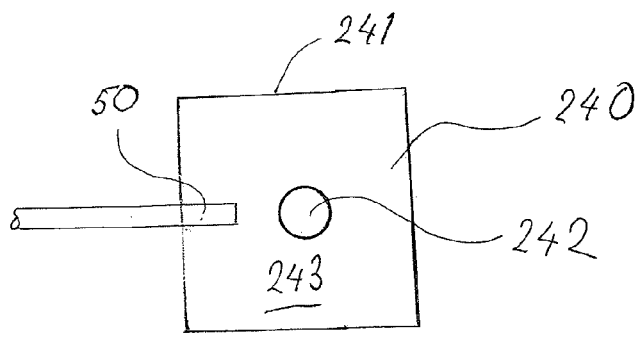
FIGS. 5a and 5b are schematic illustrations of a second example of the one-way valve at the inlet tube.
Figure 5B:
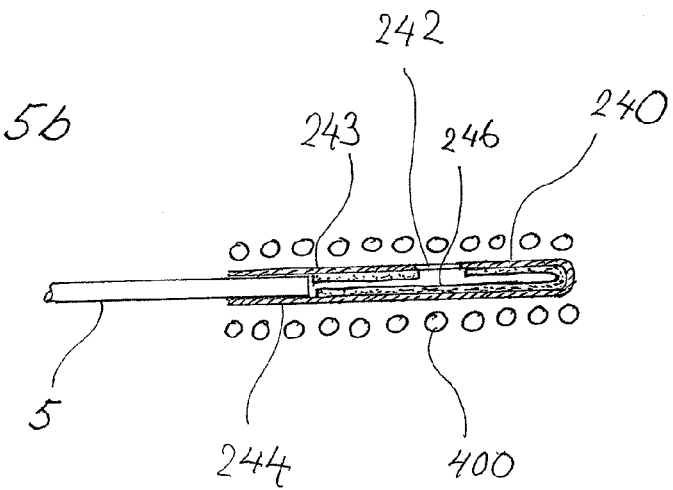

An alternative one-way valve is illustrated in FIGS. 5*a* and 5*b*.

The one-way valve 240 has the form of a bag with two main sides 243,244 and closed around its periphery 241 and sealed around the tube end for forming a bag inlet from the tube to the bag. The bag has an opening 242 on one 243 of said sides. The one-way valve is open with the two main sides at a distance from each other for allowing gas and liquid from the wound to pass into the bag via said bag inlet and out through said bag opening when the pressure around the bag is lower than at the wound. The one-way valve is closed with said main sides 243,244 pressed against each other around said bag opening when the pressure around the bag is higher than at the wound. The one-way valve 240 is shown in cross-section in FIG. 5*b*.

A shield 400, which fulfil the same purpose as the tube 40 in the embodiment according to FIGS. 4*a* and 4*b*, is schematically shown only in FIG. 5*b*, defines a space within which the bag can freely expand effected only by the pressure difference between the wound and the reservoir. The shield should be relatively form-stable and withstand mechanical pressure of sizes which can occur in the reservoir during use. The bag is preferably formed from a PUR-film with a thickness of about 20 μm and coated with a hydrophobic silicone gel layer of thickness of 40 g/m² on the sides which forms the inside of the bag. In FIG. 5*b* the silicone gel layer is designated with 246. As in the embodiment according to FIGS. 4*a* and 4*b* the silicone gel layer on the opposite main sides adheres against each other and forms a tight seal around the opening when the main sides 242 and 243 are pressed together.

Figure 6:
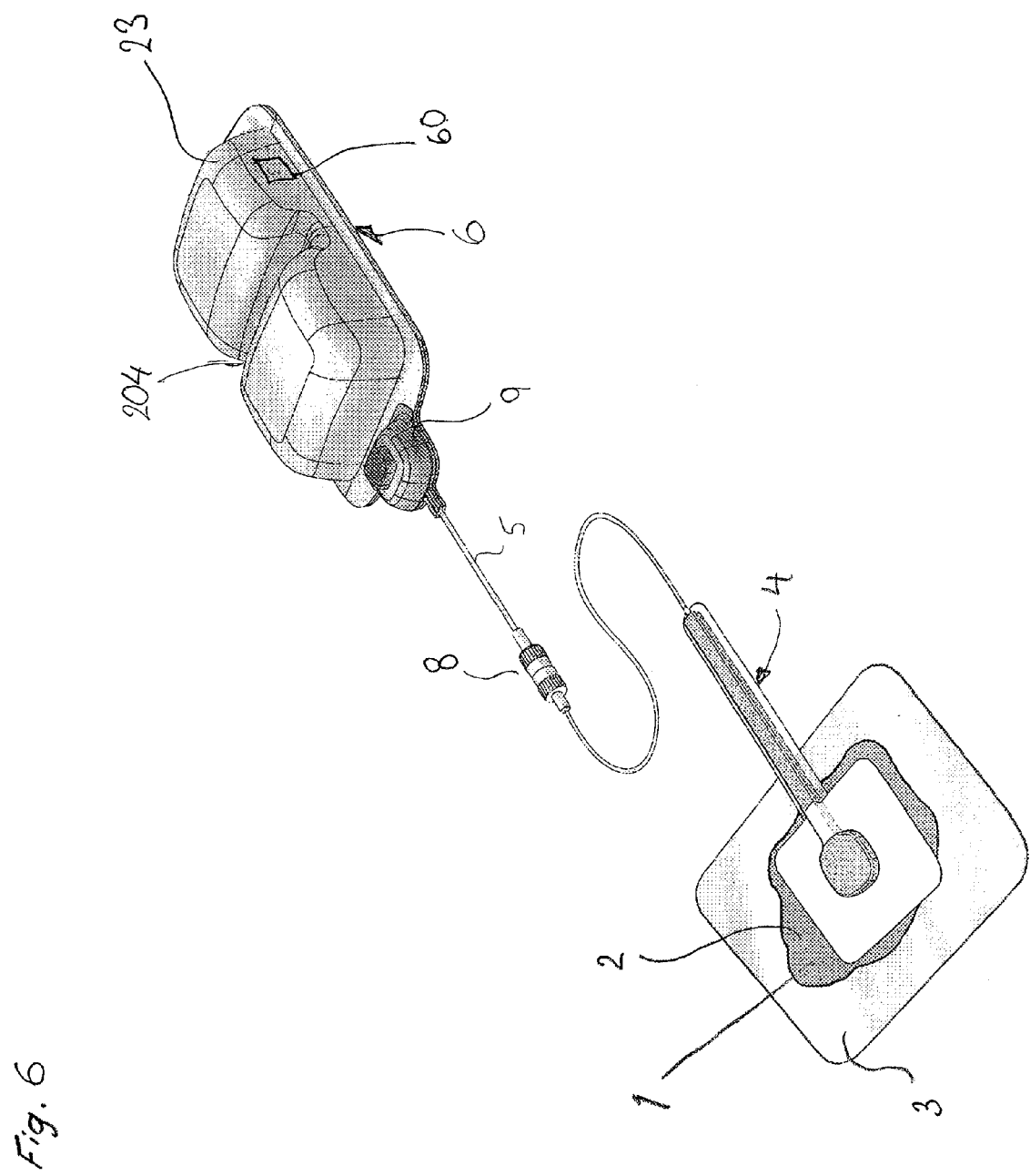
FIG. 6 shows schematically a second embodiment of the device in accordance with the invention.

In the embodiment according to FIG. 6 parts which corresponds to the same parts as in FIG. 1 has been provided with the same reference number. The reservoir 6 in the embodiment according to FIG. 6 lacks outlet tube and is not connected to an external pump. The remaining of the reservoir is formed as described in connection with FIG. 2 except for that a second one-way valve 60 is arranged in the cover, for instance in the plastic film 23 as indicated.

The first material 20 is, in the embodiment according to FIG. 6, arranged to serve as said suction unit and is capable of providing a reduced pressure upon manual compression. The second one-way valve 60 is arranged in the cover for allowing gas to flow out from said suction unit during compression but not in the opposite direction.

In a preferred embodiment the first material is an open-cell foam, that has a hinge 204 along which the foam can be bended and in the second and third material and the cover are arranged to allow said bending. The hinge is arranged to mechanically divide the reservoir in two parts and the reservoir is foldable along said hinge for facilitate manual compression of the compressible first material.

When treating wounds with a wound cavity it is for the healing important to fill up the cavity with a wound pad. It is also important that such a wound pad is hydrophobic in order to avoid that wound fluid is absorbed and held in the wound pad. A further requirement of such a wound pad is that the pad does not stick to the wound tissue. This is a serious problem with conventional wound pad, such as gauze, and the consequence is that the wound is damaged when the pad is changed. This problem can to some extent be avoided by wetting the gauze with saline. A further drawback with conventional wound pad, such as gauze, is fibre linting. Detached fibres stick to the wound, which in turn may cause inflammation.

It is earlier known to use open-cell foam as wound pad. The use of open-cell polymeric foam is described in for instance U.S. Pat. No. 5,636,643, mentioned above. The wound pad according to the present invention is significantly improved in that the foam is fully impregnated with a soft hydrophobic silicone gel. The advantage with the silicone gel is that the impregnated open-cell wound pad can be more easily removed from the wound compared to a wound pad of an open-cell foam without silicone gel. It is important that the foam is fully impregnated with silicone gel, i.e. that silicone gel is spread all through the foam. It is advantageous for the cell growth, i.e. healing of the wound, that cell can grow into the pores of the open-cell foam. Possible draw-back with conventional open-cell foam is that the in-growth cell can get stuck in the pores of the foam and that the healing is disturbed when the pad is removed. This risk is eliminated when the foam is fully impregnated with a hydrophobic silicone gel. A further advantage with a foam impregnated with silicone gel compared with a foam without silicone gel is that with an impregnated foam the risk is practically eliminated that wound fluid get stuck in the wound pad and leaks back to the wound. Another advantage with the fully impregnation of the foam pad with silicone gel is that the risk is practically eliminated that foam particles loosen from the pad and get stuck in the wound. The silicone gel reinforces the structure. Without silicone gel there is a risk that foam fragments could detach when the pad is cut to fit in a wound cavity.

Examples of suitable foams are reticulated foams on polyester or polyether basis.

An example of a suitable silicone gel is a gel formed from the two components: Wacker Elastosil 45554 Part A and Wacker Elastosil 45554 Part B. Which components are sold under said trade name by Wacker.

It is important that the foam is sufficiently soft so that it does not press hard against the wound surface and hurt the patient but it must also be sufficiently stiff so that the wound cavity is supported by the foam. The hardness of the foam should preferably be between 1.0-6.0 kPa, and more preferably 1.5-5.0 kPa measured according to ISO 3386-1 at 40% compression.

The density of the foam is preferable between 20-40 kg/m$^3$, and more preferably between 25-35 kg/m$^3$ measured according to ISO 845. The foam must also have certain elasticity to perform well as a wound pad intended to fill a wound cavity. Preferably the foam has at 25% elongation a wet elasticity higher than 6kPa, (obtained by dividing the measured force 1.5 N with the surface area (0.015 m×0.015 m) 225×10$^{-6}$ m$^2$) of the wet test sample and a dry elasticity higher than 13 kPa (obtained as dividing the measured force 1.5 N with the surface area (0.015 m×0.015m) 225×10$^{-6}$ m$^2$) measured according to a method described in Appendix A.

A suitable cell diameter of the open-cell foam is between 500-1800 μm, and preferably 1100-1500 μm measured according to Visiocell SS-T.013.4E. Foam of this type is sold by for instance the Belgian firm Recticel.

The device has above been described in connection with treatment of wound at negative pressure, i.e. with use of an electrical or manual pump.

Figure 7:
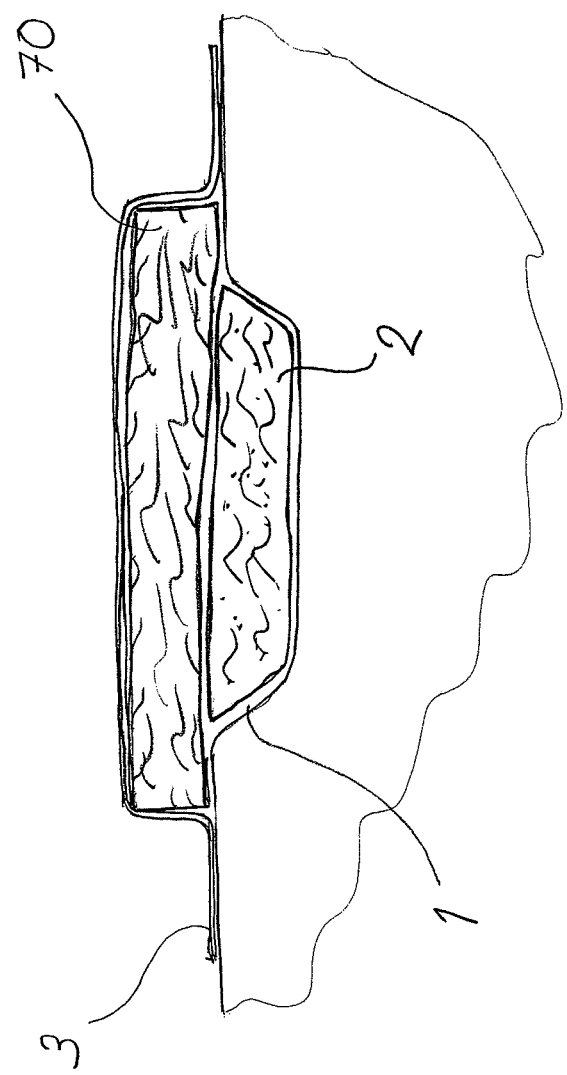
FIG. 7 shows schematically a third embodiment of the device in accordance with the invention.

The inventive concept is however the specific open cell foam, which is fully impregnated with a silicone gel. As is shown schematically in FIG. 7 the wound pad 2 can be used in a wound together with just an absorbent member 70, which sucks wound fluid from the wound through the open-cell wound pad 2, which is fully impregnated with the silicone gel. A sealing film 3 is arranged over the absorbent member and adhered to the skin around the wound.

Figure 8:
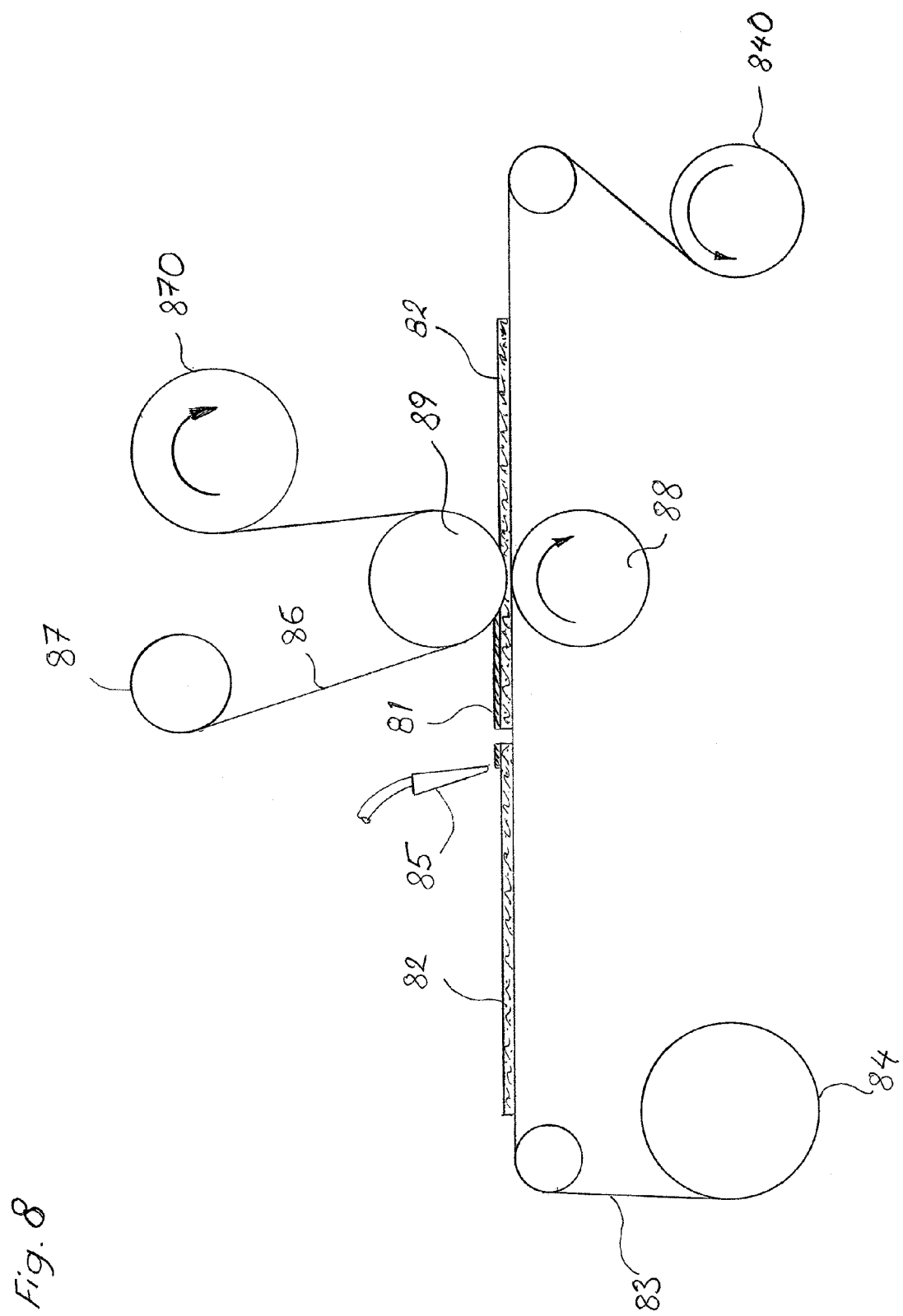
FIG. 8 illustrate schematically a method for manufacturing of the wound pad in accordance with the invention.

In FIG. 8 is illustrated an example over the method for fully impregnation of an open-cell foam.

A web 82 of open-cell foam is transported on a paper web 83 fed from a roll of paper 84. The silicone gel 81 is in an uncured state applied via a nozzle 85 on one side of the web 82 of the open-cell foam. The web 82 with the applied silicone gel is fed between two webs of process paper, the paper web 83 and a further paper web 86 from the paper roll 87, through a pair of press rolls 88 and 89. The foam with the applied silicone gel is squeezed between the press rolls for distributing the gel over the total cross section of the foam. The paper web 86 is after use rolled up on the roll 870 and the paper web 83 is after use rolled up on the roll 840. The two paper webs are hydrophilic and can absorb silicone gel. It is important that excessive silicone gel from the foam web is removed from the foam web. With this process a foam fully impregnated with silicone gel is achieved where the gel is homogenously distributed all through the foam. The foam web is thereafter heated for curing of the silicone gel. The curing of the silicone may be performed in a host blast furnace at a temperature of about 100° C. during about 1-5 minutes, preferably about 3 minutes.

The pressure between the press rolls is about 5 bar and said pressure is adjustable for optimal impregnation. Control of full impregnation of the foam web can be performed by inspecting the two webs of process paper. Both paper webs are coated with silicone gel when the foam web is fully impregnated.

The velocity of the webs through the press rolls is about 2-5 m/min, preferably about 3 m/min.

A reliable way of controlling that the open-cell foam is fully impregnated with silicone gel is to take photos with an Electron Probe Micro Analyser of the type Energy Dispersive Spectrometer also known under the abridgment EPMA/EDS and then observing the electron-photos. The principle of said device is to measure the energy of X-rays quanta for determining elements present in a sample. Example of such instrument is JEOL, model JXA-8600.

Figure 9:
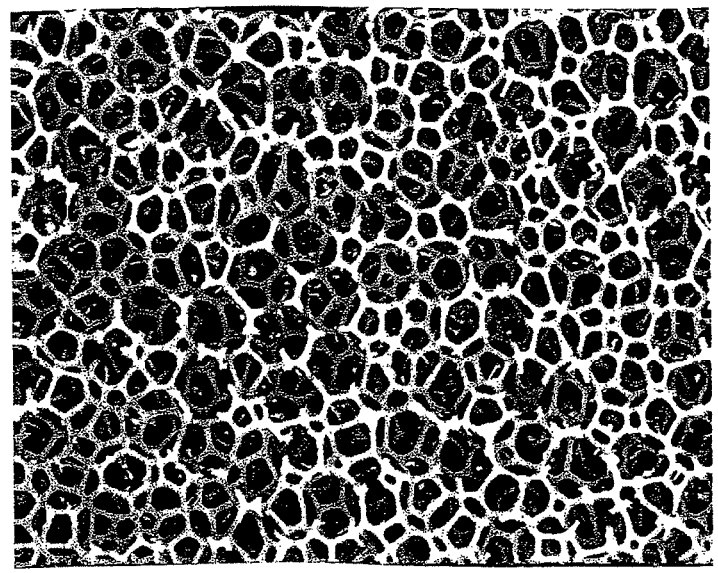
FIG. 9 is an electron image of an example of the impregnated foam according to the invention.
Figure 10:
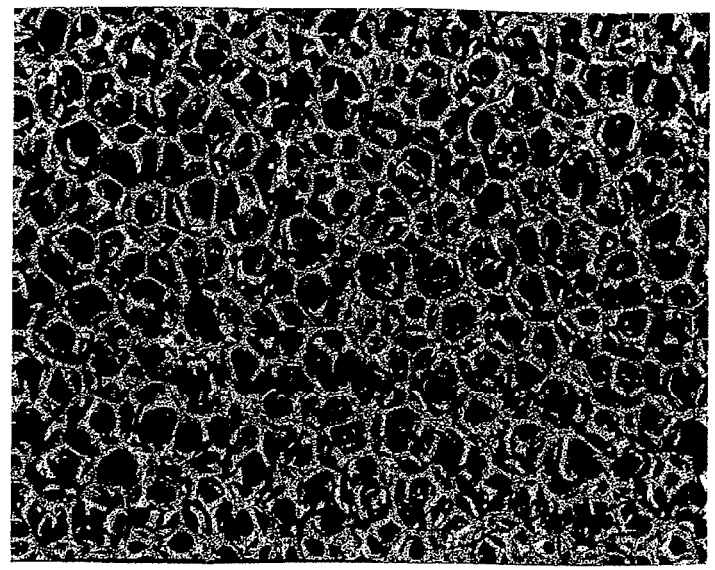
FIG. 10 is a similar picture as in FIG. 9 but showing the distribution of silicone gel over the cross-section.

FIG. 9 is an electron image taken with such instrument of the impregnated foam of the type as described above. FIG. 10 shows the similar picture but at an energy that shows the distribution of the silicone gel in the open-cell foam. As is clearly shown in FIG. 10 the silicone gel is distributed all over the cross section of the foam.

The present invention is not limited to the embodiment described above, but a large number of modifications are possible within the scope of the patent claims below.

In the description above and in the following claims all values on hardness, density and elongation are given for the non-impregnated foam.

Density is the one parameter which is most affected by impregnation. The density after being fully impregnated could even be about doubled.

Hardness, elongation and most likely also poor size are nearly unaffected by the impregnation.

Appendix A
Test Method
Tensile Force and Elongation
1 Reference Method
   ASTM D 882-02
   Deviation: The force is measured at different elongations and in addition on other materials than film
2 Purpose
   To determine the tensile force at different elongation.
3 Principle
   A strip of specified size is elongated until defined elongation.
4 Preparation of Test Pieces
   Material required—Preferable the whole width and at least 30 cm.
   Number of measurements—5 pieces
     Preparation—Punch out test pieces from the whole width of the material.
     —Use the punch 25×200 mm.
     —Conditioning At 23±2° C. and (50±2) % RH during at least 4 hours.
5 Equipment
   Press, forming punch 25×200 mm with associated punch plate.
   Tensile tester, Alliance
6 Procedure
   Running adjustment:
   Gauge length—100 mm
   Cross head speed—42 mm/minute
   Chose at what elongation the force is to be measured, 2, 5, 10, 15, 20 or 25% elongation.

Place the test strip into the upper clamp of the tensile tester. Make sure that it hangs vertically.

Then fasten it at the lower clamp. Make sure that the test strip is not elongated.

Start the tensile tester.

7 Calculations

Measure the thickness of the test pieces. Calculate the cross-section area in $m^2$. Calculate the mean value and the standard deviation for the force in N at the chosen elongation. Divide the force with the cross-section area of the test sample to obtain the result in kPa.

9 Reporting

Method and deviations

Material and origin

Sample designation

Number of measurements

Mean value and standard deviation for the chosen elongations.

The invention claimed is:

1. A method for manufacturing of a wound pad of an open-cell polyurethane foam that is impregnated with a soft hydrophobic silicone gel comprising the steps of:

applying silicone gel in an uncured state on one side of a web of an open-cell polyurethane foam, feeding said web with the applied silicone gel between two webs of process paper through a pair of press rolls, squeezing between the press rolls the foam with the applied silicone gel for distributing the gel over the total cross section of the foam, removing said two webs of process paper with excessive silicone gel from the foam web, and heating the foam web thereafter for curing of the silicone gel.

2. A method according to claim 1, wherein the curing of the silicone gel is performed in a hot blast furnace at a temperature of about 100° C. during about 1-5 minutes.

3. A method in accordance with claim 1, wherein the pressure between the press rolls is about 5 bar and that said pressure is adjustable for optimal impregnation and that control of full impregnation of the foam web is performed by inspecting the two webs of process paper, which both paper webs are coated with silicone gel when the foam web is fully impregnated.

4. A method in accordance with claim 1, wherein the velocity of the webs through the press rolls is about 2-5 m/min.

* * * * *

UNITED STATES PATENT AND TRADEMARK OFFICE
CERTIFICATE OF CORRECTION

PATENT NO. : 8,469,915 B2  Page 1 of 1
APPLICATION NO. : 12/936754
DATED : June 25, 2013
INVENTOR(S) : Johannison et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 111 days.

Signed and Sealed this
Eighth Day of September, 2015

Michelle K. Lee
*Director of the United States Patent and Trademark Office*